United States Patent
McNair

(10) Patent No.: US 11,452,652 B1
(45) Date of Patent: Sep. 27, 2022

(54) PREDICTING AND PREVENTING CAREGIVER MUSCULOSKELETAL INJURIES

(71) Applicant: CERNER INNOVATION, INC., Kansas City, KS (US)

(72) Inventor: Douglas S. McNair, Leawood, KS (US)

(73) Assignee: CERNER INNOVATION, INC., North Kansas City, MO (US)

(*) Notice: Subject to any disclaimer, the term of this patent is extended or adjusted under 35 U.S.C. 154(b) by 637 days.

(21) Appl. No.: 15/824,765

(22) Filed: Nov. 28, 2017

Related U.S. Application Data

(60) Provisional application No. 62/427,087, filed on Nov. 28, 2016.

(51) Int. Cl.
| | | |
|---|---|---|
| G06F 17/10 | (2006.01) | |
| A61G 7/10 | (2006.01) | |
| G06Q 50/22 | (2018.01) | |
| A61B 5/00 | (2006.01) | |
| A61G 7/00 | (2006.01) | |
| G16H 50/70 | (2018.01) | |

(52) U.S. Cl.
CPC .............. *A61G 7/10* (2013.01); *G06Q 50/22* (2013.01); *A61B 5/7275* (2013.01); *A61B 5/746* (2013.01); *A61B 5/7465* (2013.01); *A61G 7/001* (2013.01); *G16H 50/70* (2018.01)

(58) Field of Classification Search
CPC . G06F 17/40; G06F 8/35; G06F 40/44; G06F 2111/08; G06F 11/3452; G06F 19/00; G06F 17/30; A61G 7/10; A61G 7/001; A61B 5/7275; A61B 5/746; A61B 5/7465; G06Q 50/22
See application file for complete search history.

(56) References Cited

U.S. PATENT DOCUMENTS

| | | |
|---|---|---|
| 5,012,819 A | 5/1991 | Marras et al. |
| 5,094,249 A | 3/1992 | Marras et al. |
| 5,143,088 A | 9/1992 | Marras et al. |
| 8,529,448 B2 | 9/2013 | McNair |

(Continued)

OTHER PUBLICATIONS

Weitz A Comparative Analysis Between Skilled Nursing Facilities Experiencing High Versus Low Resident Transfer Injury Rates University of Tennessee at Chattanooga (Year: 2010).*

(Continued)

*Primary Examiner* — Rehana Perveen
*Assistant Examiner* — Cuong V Luu
(74) *Attorney, Agent, or Firm* — Shook, Hardy & Bacon L.L.P.

(57) ABSTRACT

Systems, methods and computer-readable media are provided for determining the modality for transferring, lifting, or repositioning (TLR) a human patient in a health care setting contexts. In some cases, a model-based recursive partitioning and Bradley-Terry regression is applied, which may be optionally parallelized so as to determine statistical associations with various factors, such as caregiver attributes, care venue, and patient attributes. One embodiment determines a Bradley-Terry regression model from the recursive partitioning which may be incorporated into a TLR selection decision-support tool or otherwise utilized to identify the optimal modality.

19 Claims, 14 Drawing Sheets

(56) References Cited

U.S. PATENT DOCUMENTS

| | | |
|---|---|---|
| 2010/0036287 A1 | 2/2010 | Weber |
| 2010/0121227 A1 | 5/2010 | Stirling et al. |
| 2011/0067253 A1 | 3/2011 | Happel |
| 2014/0031969 A1* | 1/2014 | Baseman ......... G05B 19/41875 700/121 |
| 2014/0176944 A1 | 6/2014 | Addison et al. |
| 2015/0193583 A1* | 7/2015 | McNair ................. G16H 50/20 705/2 |
| 2015/0254330 A1* | 9/2015 | Chan .................... G06F 16/219 707/613 |
| 2015/0272504 A1 | 10/2015 | Giancardo |
| 2017/0228651 A1 | 8/2017 | Yamamoto |
| 2017/0296129 A1 | 10/2017 | Petterson et al. |

OTHER PUBLICATIONS

Wilcox et al. Comparing Two Dependent Groups Via Quantiles Journal of Applied Statistics, Dec. 2012 (Year: 2012).*

Strobl et al. Accounting for Individual Differences in Bradley-Terry Models by Means of Recursive Partitioning Journal of Educational and Behavioral Statistics, 2011 (Year: 2011).*

Torelli et al. Advances in Theoretical and Applied Statistics Springer-Verlag Berlin Heidelberg, 2013 (Year: 2013).*

Black et al. Effect of Transfer, Lifting, and Repositioning (TLR) Injury Prevention Program on Musculoskeletal Injury Among Direct Care Workers Journal of Occuprational and Environmental Hygiene, 8 pp. 226-235 (Year: 2011).*

Marras, William S., "The Working Back: A Systems View", Wiley-Intersciences, 2008, 9 pages.

U.S. Appl. No. 15/713,158, filed Sep. 22, 2017, titled "Determining Health Service Performance Via A Health Exchange", inventor Douglas S. McNair.

Glickman Mark E., Parameter estimation in large dynamic paired comparison experiments. Appl Stat 1999; 48(Pt 3):377-94.

"Package RSpinCalc manual", Available Online at: <https://cran.r-project.org/web/packages/RSpincalc/RSpincalc.pdf>, Jul. 17, 2015, 34 pages.

Preinterview First Office Action received for U.S. Appl. No. 15/847,597, dated Jun. 5, 2020, 4 pages.

Final Office Action received for U.S. Appl. No. 15/847,597, dated May 17, 2021, 16 pages.

* cited by examiner

FIG. 3A — RAW COUNTS FOR TLR METHODS' USAGE OF DEVICES

| sl | sa | tr | cg |
|---|---|---|---|
| 0 | 19 | 30 | 67 |
| 1 | 15 | 28 | 71 |
| 0 | 8 | 27 | 66 |
| 0 | 5 | 38 | 69 |
| 0 | 12 | 31 | 77 |
| 0 | 6 | 29 | 83 |
| 1 | 10 | 41 | 70 |
| 0 | 8 | 30 | 51 |
| 0 | 9 | 28 | 74 |
| 1 | 11 | 34 | 83 |
| 0 | 15 | 38 | 73 |
| 0 | 7 | 24 | 69 |
| 0 | 15 | 27 | 64 |
| 0 | 11 | 30 | 62 |
| 0 | 17 | 49 | 67 |
| 1 | 15 | 35 | 66 |
| 0 | 16 | 25 | 62 |

FIG. 3B — TRANSFORM COUNTS TO PAIRED COMPARISONS MATRIX

| sl_sa | sl_tr | sl_cg | sa_tr | sa_cg | tr_cg | con1 | con2 | con3 |
|---|---|---|---|---|---|---|---|---|
| -2 | -2 | -2 | -1 | -1 | -1 | 0 | 0 | 1 |
| -2 | -2 | -2 | -1 | -1 | -1 | 0 | 0 | 1 |
| -2 | -2 | -2 | -1 | -1 | -1 | 0 | 0 | 1 |
| -2 | -2 | -2 | 0 | 0 | 0 | 0 | 1 | 0 |
| -2 | -2 | -2 | 0 | -1 | 0 | 1 | 0 | 0 |
| -2 | -2 | -2 | 0 | 0 | 1 | 0 | 0 | 2 |
| -2 | -2 | -2 | 0 | -1 | 0 | 0 | 0 | 2 |
| -2 | -2 | -2 | 0 | 0 | 0 | 0 | 0 | 2 |
| -2 | -2 | -2 | 1 | 1 | 1 | 0 | 1 | 1 |
| -2 | -2 | -1 | 1 | 0 | 0 | 0 | 1 | 1 |
| -2 | -2 | -1 | 0 | 1 | 1 | 0 | 2 | 1 |
| -2 | -2 | -2 | 1 | 0 | 1 | 0 | 2 | 0 |
| -2 | -2 | -2 | 0 | -1 | 0 | 1 | 0 | 0 |
| -2 | -2 | -2 | 1 | 1 | 1 | 1 | 0 | 1 |
| -2 | -2 | -2 | -1 | -1 | 0 | 0 | 1 | 2 |
| -2 | -2 | -2 | -1 | -1 | 1 | 0 | 1 | 2 |
| -2 | -2 | -2 | 0 | 0 | 1 | 0 | 1 | 2 |

EXAMPLE OF PATIENT CONTEXT AND SCORING

| FACTOR | FACTOR | POINTS |
|---|---|---|
| PATIENT WEIGHT | >120 KG | 2 |
| PATIENT BMI | >32 KG/M2 | 2 |
| PATIENT AGE | >75 YR | 1 |
| PATIENT BRADEN SCORE | >13 | 2 |
| PATIENT CHARLSON COMORBIDITY INEX | >5 | 2 |
| PATIENT KARNOFSKY SCORE | <60 | 1 |
| PATIENT CLAIRVIA ACUITY | >9 | 1 |
| PATIENT APS | >30 | 1 |
| PATIENT DAYS POST-OP | <2 | 2 |
| PATIENT POST-OP DELIRIUM | Y | 1 |
| PATIENT MOBILIZATION AFTER SURGICAL OR INVASIVE MEDICAL... | Y | 1 |
| PATIENT ON MONITOR OR INFUSION PUMP OR OTHER DEVICE | Y | 1 |
| PATIENT MMSE | <15 | 1 |
| PATIENT WILLING AND ABLE TO FOLLOW INSTRUCTIONS | N | 1 |
| PATIENT HX FALL | Y | 2 |
| PATIENT HX SYNCOPE | Y | 1 |
| PATIENT MAJOR DEPRESSIVE DISORDER | Y | 1 |
| PATIENT PSYCHOSIS | Y | 1 |
| PATIENT ANTIHYPERTENSIVE RX | Y | 1 |
| PATIENT ANTICHOLINERGIC RX | Y | 1 |
| PATIENT OPIATE RX | Y | 1 |
| PATIENT BENZODIAZEPINE RX | Y | 1 |
| PATIENT NUMBER OF MEDS ON-BOARD | >5 | 2 |

*FIG. 4A*

EXAMPLE OF CAREGIVER CONTEXT AND SCORING

| FACTOR | CONDITION | POINTS |
|---|---|---|
| NURSE BMI | > 30 KG/M2 | 1 |
| NURSE HX PREVIOUS INJURY | Y | 1 |
| NURSE AGE | BETW 19 AND 55 | 1 |
| NURSE ROLE (CAN, RN, NP, OTHER) | CNA | 2 |
| NURSE YEARS IN PRACTICE | <2 | 2 |
| NURSE MONTHS AT THS INSTITUTION | >6 | 1 |
| NURSE MONTHS IN THIS ROLE | <12 | 1 |
| NURSE ADVANCE PRACTICE CREDENTIAL OR GRAD DEGREE | N | 1 |
| NURSE FREQUENCY OF LIFTS PER 100 SHIFTS | >50 | 1 |
| NURSE NUMBER OF LIFTS IN PAST 3 SHIFTS | >7 | 1 |
| NURSE WORKING DOUBLE SHIFT | Y | 1 |

FIG. 4B

EXAMPLE OF ADDITIONAL CONTEXT AND SCORING

| FACTOR | CONDITION | POINTS |
|---|---|---|
| UNIT TYPE | NEURO, ORTHO, ICU, ... | 1, 2, 3 |
| UNIT P:N RATIO ON CURRENT SHIFT, AS A QUANTILE OF HISTORICAL | >0.90 | 2 |
| UNIT BASELINE MSI RATE (INJ PER YEAR PER 100 FTE) | >5.6 | 1 |
| SHIFT | EVENING | 1 |
| SHIFT LENGTH | 12 HR | 1 |

FIG. 4C

```
###########################################################################

#   Model-based recursive partitioning (MOB) discovery of clusters for subsequent BT modeling

##################################################################### library(MASS)
library(zoo)
library(grid)
library(sandwich)
library(survival)
library(strucchange)
library(partykit)
library(psychotools)
library(psychotree)
library(fitdistrplus)

# function defs
btfit1 <- function(y, x=NULL, start=NULL, weights=NULL, offset=NULL, ...) {
  btReg.fit(y, ...)
} worthf <- function(info) {
   paste(info$object$labels, format(round(worth(info$object), digits=3)), sep = ": ")
} estfun.btReg <- function(x, ...) {
  x$estfun
} load raw counts data - example con[] = [0,0,1]
dat2 <- read.csv(file="c:/0_cerdsm/IP/occupational_health_nsg_lift_inj/dat2.csv", header=TRUE,
colClasses=rep("integer",4))
# counts for alternative transfer-lift-reposition methods on 500 consecutive days in 41 med-surg
units:  sl, sa, tr, cg analyze raw counts data to determine Poisson distribution lambda values for each choice
lambda <- rep(0,4)
for (i in 1:4) {
  fit <- fitdist(dat2[,i], "pois", method="mle")
  lambda[i] <- fit$estimate
}
```

.
.
.

CONTINUES IN FIG. 6B

*FIG. 6A*

CONTINUES FROM FIG. 6A

.
.

```
# determine Skellam Poisson-difference quantiles
n1 <- 1000
n2 <- 1000
preference <- rep(0,6)

# set X1 choice less-preferred than X2
set.seed(1239)
theta <- matrix(rep(rep(0, n1),n2), nrow=n1)

X1 <- rpois(n1, lambda[1])
X2 <- rpois(n2, lambda[2])
for (i in 1:1000) {
   XX1 <- sample(X1, n1, repl=T)
   XX2 <- sample(X2, n2, repl=T)
   theta[i,] <- XX1 - XX2
} a <- rep(0,n1)
for (i in 1:1000) {
  a[i] <- quantile(theta[i,], 0.025) # Efron bootstrap
}
a <- mean(a)

p.sk <- (1 - pskellam(a, lambda[1], lambda[2], lower.tail=FALSE))/2 transform quantiles to symmetric preference scale
score <- 0
if (p.sk < 0.05) {
    score <- -2
  } else if (p.sk < 0.25) {
    score <- -1
  } else if (p.sk < 0.75) {
    score <- 0
  } else if (p.sk < 0.95) {
    score <- 1
  } else {
    score <- 2
}
preference[1] <- score continue for 5 remaining combinations
(lambda[1]:lambda[3]; lambda[1]:lambda[4]; lambda[2]:lambda[3]; lambda[2]:lambda[4];
lambda[3]:lambda[4])

# store transformed data
x <- data.frame(cbind(sl_sa=preference[1], sl_tr=preference[2], sl_cg=preference[3],
sa_tr=preference[4], sa_cg=preference[5], tr_cg=preference[6])
write.csv(x, file="c:/0_cerdsm/IP/occupational_health_nsg_lift_inj/dat3a.csv")
```

.
.

CONTINUES IN FIG. 6C

*FIG. 6B*

CONTINUES FROM FIG. 6B

.
.

```
# load transformed preferences-coded data
dat3 <- read.csv(file="c:/0_cerdsm/IP/occupational_health_nsg_lift_inj/dat3.csv", header=TRUE,
        colClasses=c(rep("integer",6),rep("factor",3)))

# note: Likert scales not yet implemented in function btReg.fit(),
# so for the time being transform integer factor values to binomial
# cast preferences as paired-comparison matrix
# positive values indicate that the first object was preferred
# negative values indicate that the second object was preferred
# zero values indicate no preference between the two objects
# larger absolute values indicate stronger preference
mat2 <- as.matrix(dat3[,1:6])

# construct paired comparisons
pc5 <- paircomp(mat2, labels=c("sl","sa","tr","cg"))

# collapse Likert to >/=/< scale
mscale(pc5) <- sign(mscale(pc5))

# pc5 <- paircomp(mat2,
#          labels=c("sl","sa","tr","cg"),
#          covariates=data.frame(tlr_method=factor(c(1,1,1,2), labels=c("mechanical
assist","caregiver"))))
# covariates(pc5)

# construct data.frame for Bradley-Terry regression
dat6 <- data.frame(pref=pc5, con1=dat3[,7], con2=dat3[,8], con3=dat3[,9])
```

.
.

CONTINUES IN FIG. 6D

*FIG. 6C*

CONTINUES FROM FIG. 6C

.

.

```
# determine Bradley-Terry model by model-based recursive partitioning (MOB method)
ctrl <- mob_control(alpha=0.1, bonferroni=TRUE, minsize=1, maxdepth=4,
  mtry=100, trim=0.1, breakties=TRUE, parm=NULL, dfsplit=TRUE, prune=NULL,
  restart=TRUE, verbose=FALSE, caseweights=TRUE, ytype="vector", xtype="matrix",
  terminal="object", model=TRUE, numsplit="left",
  catsplit="binary", vcov="opg", ordinal="chisq", nrep=1000,
  minsplit=5, minbucket=5, applyfun=NULL, cores=NULL)
bt1 <- mob(pref ~ 1 | con1 + con2 + con3, data=dat6, fit=btfit1, control=ctrl)

# examine BT model properties
bt1
coef(bt1)
logLik(bt1)

# construct model based only on patient context parms
bt2 <- mob(pref ~ 1 | con1, data=dat6, fit=btfit1, control=ctrl)
bt2
# Fitted party:
# [1] root
# |   [2] con1 in 0, 1, 2
# |   |   [3] con1 in 0, 1
# |   |   |   [4] con1 in 0: n = 116
# |   |   |          sl        sa       tr (undecided)
# |   |   |       0.1590754 1.1388318 1.3106499 -0.3714331
# |   |   |   [5] con1 in 1: n = 69
# |   |   |          sl        sa       tr (undecided)
# |   |   |       0.22648208 1.08803323 1.26678167 0.08160011
# |   |   [6] con1 in 2: n = 54
# |   |          sl        sa       tr (undecided)
# |   |       1.7231892 1.7574168 1.2173961 0.3791159
# |   [7] con1 in 3, 4, 5, 6: n = 110
# |          sl        sa       tr (undecided)
# |       4.4092547 3.1205806 1.8018793 0.2425643

# Number of inner nodes:    3
# Number of terminal nodes: 4
# Number of parameters per node: 4
# Objective function: 1970.359
```

.

.

CONTINUES IN FIG. 6E

*FIG. 6D*

CONTINUES FROM FIG. 6D

.
.

```
# determine adequacy of model via strucchange
sctest(bt2, node=1)
#            con1
# statistic 1.671840e+02
p.value   1.993042e-23 sctest(bt2, node=2)
con1
# statistic 4.548023e+01
p.value   2.983737e-07 sctest(bt2, node=3)
con1
# statistic 10.41433604
p.value   0.03399767 sctest(bt2, node=7)
con1
# statistic 17.9852510
# p.value   0.1161391

# In node 3, no further significant parameter instabilities can be detected and hence partitioning
stops in that branch.

# construct plots of model performance
plot(bt2, FUN=worthf)
par(mfrow=c(2, 2))
nodeapply(bt2, ids=c(2, 4, 6, 7), FUN=function(n) plot(n$info$object, main=n$id, ylim=c(0, 0.4)))

# predict classifications for new cases using BT model
# tm <- data.frame(con1=factor(c(0,2,4)), con2=factor(c(3,2,5)), con3=factor(c(1,1,7)))
tm <- data.frame(con1=factor(c(0,2,4)))
predict(bt2, tm, type="node")
# 1  2  3
# 4  5  6
# tr tr sa
```

*FIG. 6E*

PREDICTING AND PREVENTING CAREGIVER MUSCULOSKELETAL INJURIES

CROSS-REFERENCE TO RELATED APPLICATIONS

This application claims the benefit of U.S. Provisional Application No. 62/472,087; entitled "Predicting and Preventing Caregiver Musculoskeletal Injuries," filed Nov. 28, 2016, which is expressly incorporated by reference in its entirety.

BACKGROUND

Occupational health research has shown that certain worker and job characteristics are risk factors for workplace injuries. Workers who engage in physically demanding jobs, especially those jobs that involve repetitive motion, are at greater risk for work-related musculoskeletal injury (MSI). Nurses, in particular are considered to be at high risk of workplace MSI compared to other health care workers. Musculoskeletal injuries and symptoms are prevalent in nurses and are largely associated with strenuous patient handling. It is also associated with frequent patient handling, including: transferring, lifting, and/or repositioning (TLR) maneuvers with patients.

One recent study indicated patients with a body mass index of less than or equal to 35 kg/m2 constituted less than ten percent of the patient population. However, 29.8% of staff injuries related to patient handling were linked to working with a bariatric patient. Bariatric patient handling accounted for 27.9% of all lost workdays and 37.2% of all restricted workdays associated with patient handling. Nursing assistants and registered nurses accounted for 80% of the injuries related to bariatric patient handling. Turning and repositioning the patient in bed accounted for 31% of the injuries incurred. In another recent study, one-third (n=876) of all musculoskeletal injuries resulted from patient handling activities. Most (83%) of the injury burden was incurred by inpatient nurses' aides, registered nurses, and radiology technicians. Injury rates were highest for nurses' aides (8.8/100 full-time equivalent, FTEs) and smaller workgroups including emergency medical technicians (10.3/100 FTEs), patient transporters (4.3/100 FTEs), operating room technicians (3.1/100 FTEs), and morgue technicians (2.2/100 FTEs). Forty percent of injuries due to lifting/transferring patients might have been preventable were the right mechanical lift equipment used. By contrast, 32% of injuries resulted from repositioning/turning patients, pulling patients up in bed, or catching falling patients. Many such injuries are not likely to have been prevented by the use of particular lift equipment or lift methods. However, the quantitative ex ante estimation of the risk may help to reallocate resources in terms of multi-person 'lift teams,' to mitigate the risk somewhat.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

A technology is provided for determining the method and equipment that is optimal for transferring, lifting, or repositioning a human patient in any of a plurality of health care setting contexts and, for alternative methods and equipments, determining the comparative utility and risks associated with these alternatives. In particular, embodiments achieve this end from applying model-based recursive partitioning and Bradley-Terry regression, which may be optionally parallelized so as to determine statistical associations with various factors, such as caregiver attributes, care venue, and patient attributes. In an embodiment, a Bradley-Terry regression tree is determined from the recursive partitioning and utilized to identify the optimal method and equipment. Some embodiments may successfully and quickly determine this even where the number of competitors evaluated may be large. Moreover, in some embodiments, the statistical associations and coefficient values from the regressions may be utilized to predict and/or reduce the risk for musculoskeletal injury of the caregiver during patient transfer, lift, or repositioning maneuvers.

Accordingly, in an embodiment, as will be further described herein, a set of TLR methods and devices, whose optimal assignment-in-context is to be determined, are selected. A population of liftee-patients is also selected, based on inclusion-exclusion criteria and time-period, and a population of lifter-caregivers is selected; for example, the nurses on shift for a particular floor of bariatric patients. Raw count TLR usage data are received, as well as context attributes for applicable prior measurement interval(s) meeting selection criteria from the preceding steps. Context attributes, which may include a set of explanatory attribute variables, may be selectively included as independent variables in the determined models.

A statistical distribution is then determined fitting the count TLR usage data. Efron bootstrap estimation of the distributions' parameters is performed, and distribution groupings, such as quantiles, are determined for these estimated parameters. Next, the TLR modalities' raw usage counts are transformed to a Likert scale based on the quantiles or the groupings. Some embodiments may rescale the Likert scale to a smaller dynamic-range scale, if counts in some categories on the initial scale are too few. The TLR modalities usage Likert scale data is then transformed into a paired-comparisons matrix of TLR modalities to determine matches of applicable provider pairs. In an embodiment, "winner"/"loser" outcomes are rendered for applicable provider pairs.

Optimal Bradley-Terry regression model is then determined by model-based recursive partitioning on the selected explanatory attributes variables. Model convergence is then determined as well as model stability, which may be determined by structural change method. Next the statistical significance of the model's coefficients and utilities of paired-comparisons for all relevant TLR modalities pairs is determined, and the best performing (based on the statistical significance) model for selection criteria and contexts' explanatory variables and per-period TLR modalities' "winner"/"loser" outcomes for all relevant TLR modalities pairs, is stored for later use or may be implemented for utilization by a caregiver. In some embodiments, an explanatory analysis may be prepared to accompany the model, for the statistically significant associations and utilities. The model and utilities then may be incorporated into a TLR selection decision-support tool for use by authorized nursing (or other caregiver) user(s) in selecting the best TLR modality option-in-context from among alternative TLR modalities. Some embodiments integrate with other decision support tools and related tools, such as Cerner Millennium orders, Discern Expert CDS, iView, or similar applications.

In this way, a context-specific decision support tool can be provided to nurses (or other caregivers) facing TLR selection decision making In particular, a such a tool implemented using a model created according to the method embodiments described herein may be context specific with regards to the detailed attributes of the caregiver, venue, time period, and intensity, frequency, and duration of prior exposure of the prospective lifter-caregiver to lifting activity. Thus, a nurse or other caregiver is more likely to use the best available TLR method and equipment, for the particular venue and patient. Therefore, embodiments of the present disclosure also may make transfer-lift-repositioning (TLR) activities substantially safer for both the caregiver and patient. Further, embodiments can significantly facilitate compliance with Safe Patient Handling (SPH) laws, OSHA regulations, or similar regulations and policies.

BRIEF DESCRIPTION OF THE DRAWINGS

The present invention is described in detail below with reference to the attached drawing figures, wherein:

FIG. 3A depicts an example table of raw counts data for TLR methods usage of devices, which is used in an example embodiment reduced to practice and further described herein;

FIG. 3B depicts a table of transformed counts to a paired-comparisons matrix, in accordance with the example embodiment reduced to practice;

FIGS. 4A-4C depict example tables of "points" for various contexts related to patients, caregivers, and venue or other contextual factors, which may be utilized when analyzing TLR occurrences, in accordance with an embodiment of the disclosure;

FIGS. 6A-6E illustratively provide an example of a computer program routine used for determining the model for the a TLR selection decision support tool in accordance with an embodiment of this disclosure and further described in connection to FIG. 2.

DETAILED DESCRIPTION

Figure 1A:
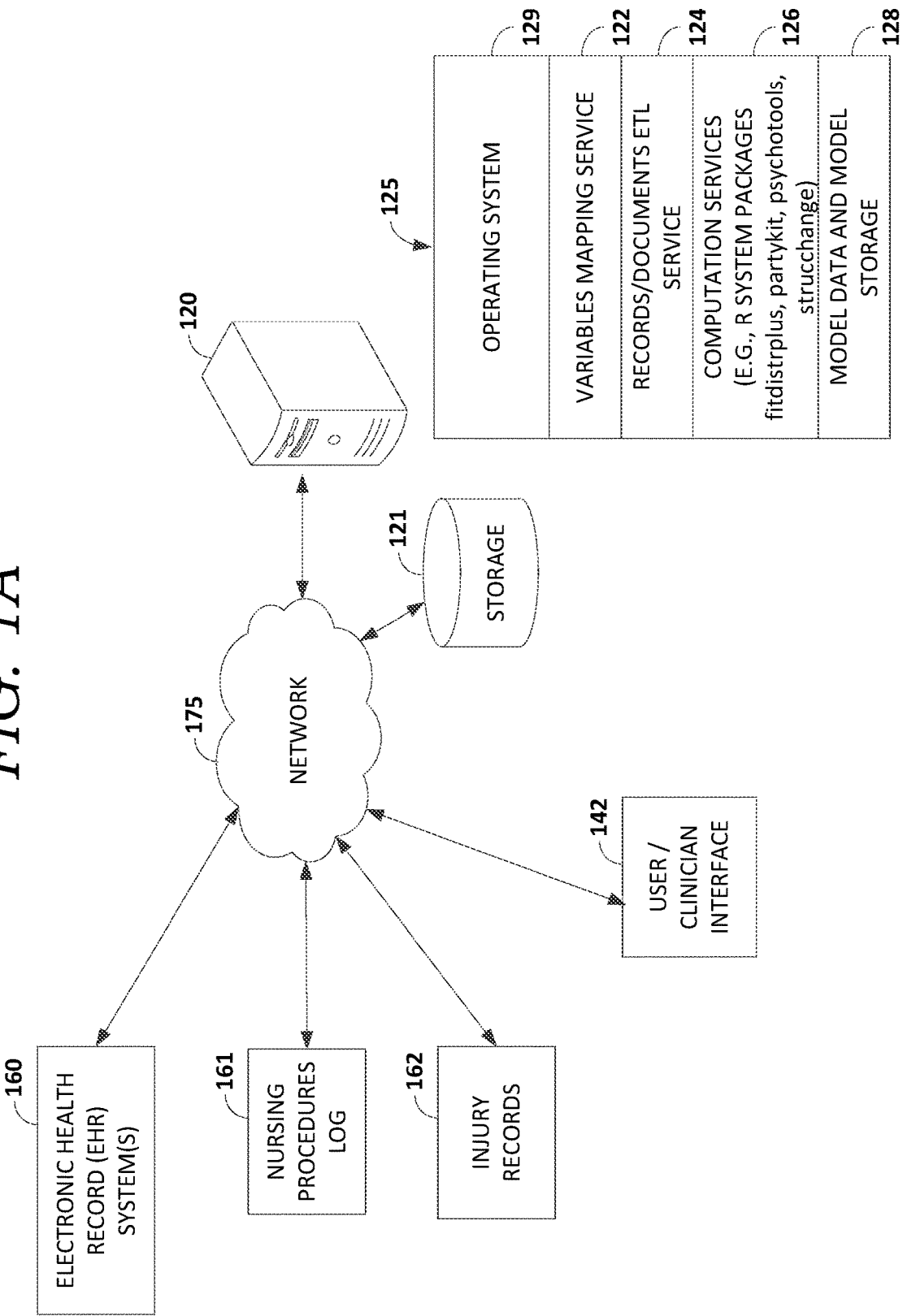
FIGS. 1A and 1B depict aspects of an illustrative architecture suitable for practicing an embodiment of the invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other computer hardware or storage devices. These technologies can store data momentarily, temporarily, or permanently. Computer storage media does not include signals per se.

As described above, workers who engage in physically demanding jobs, especially those jobs that involve repetitive motion, are at greater risk for work-related musculoskeletal injury (MSI). In particular, musculoskeletal injuries and symptoms are prevalent in nurses and are largely associated with strenuous and/or frequent patient handling including transferring, lifting, and/or repositioning (TLR) maneuvers with patients. In terms of conventional approaches to occupational health, many analyses of the physical requirements of jobs do not consider the modifying effect of frequency or time spent on a physical task and the risk of injury. One study compared the risks of MSI among workers in health care facilities based on the type of physical tasks and amount of time workers spent on such tasks. Workers who worked longer on a physical task reported more frequent and severe injuries than those who spent less time on the same physical task, performed it less frequently, or performed it with less intensity. The study found that physical tasks associated with health care jobs and the amount of time spent on these tasks constitutes serious risk factors for workplace injury. Three organizational risk factors (bed days of care, facility complexity level, and baseline MSI incidence rate) are known to be significantly associated with MSI incidence rate and explain 21% of the variation in MSI incidence. Five factors, including: (a) deployment of ceiling lifts and other new hoist and lift technologies, (b) peer leader effectiveness, (c) competency in equipment use, (d) facility coordinator link with safety committee, and (e) peer leader training, account for an additional 23% of the total variation.

Although adopting a new intervention is associated with expense, the reduction in workers' compensation costs associated with injured nurses can easily outweigh the costs of interventions. In 2011, California enacted legislation that required acute-care hospitals to implement safe patient handling (SPH) policies and programs. Recently, CDC's National Institute for Occupational Safety and Health (NIOSH), with collaborating partners, created the Occupational Health Safety Network (OHSN) to collect detailed injury data to help target prevention efforts. OHSN is a free, voluntary surveillance system for health care facilities that enables prompt and secure tracking of occupational injuries by type, occupation, location, and risk factors. One study describes OHSN findings for three types of injuries in 112 U.S. facilities reporting 10,680 OSHA-recordable patient handling events, 4,674 TLR-related injuries, and 3,972 slips, trips, and falls-related injuries occurring from Jan. 1, 2012-Sep. 30, 2014. Incidence rates for patient handling/TLR and slips, trips, and falls were 11.3 and 9.6 incidents per 10,000 worker-months, respectively. Nurse assistants and nurses had the highest injury rates of all occupations examined.

Many factors may be assessed when recommending lifting or transfer equipment or method. Some of the factors include, by way of example and not limitation, the patient's weight-bearing status, cognitive level, and upper extremity strength, and the caregiver's ability to lift more than 35 pounds. Conventional approaches to TLR decision making may consider some of these factors; however, none of the approaches is able to take into account frequency, duration, or intensity of lifting or adequately characterize risk. Additionally, none of these conventional approaches accounts for age or cumulative years of employment in nursing as predictors of risk of injury. Musculoskeletal injury claims among nurses have an incidence of approximately 5.7 claims per 100 work-years (based on a study in the Netherlands) and 6.4 claims per 100 FTE in U.S. acute-care settings. Long-term care setting incidence is event higher (13.5 per year per 100 FTE). Compared to nurses without lifts, nurses reporting high-level lift availability were half as likely to have work-related low-back pain (OR=0.50, 95% CI 0.26-0.96) and nurses reporting medium-level lift availability were 3.6 times less likely to have work-related shoulder pain (OR=0.28, 95% CI 0.09-0.91).

Significant limitations of the conventional approaches related to prediction and prevention of caregiver MSI events include that these approaches (a) are overly simplistic and not context-specific with regard to the detailed attributes of the caregiver, venue, time period, and intensity, frequency, and duration of prior exposure of the prospective lifter-caregiver to lifting activity, such that the simplistic approaches (including even procedures which may be relied on for decision support) give rise to inaccuracy, such as excessive false-positive and false-negative error rates, which result in excessive non-productive expense and failure to prevent injury, respectively). Additionally, these approaches (b) fail to take into account a variety of liftee-patient attributes beyond body weight, and do not account for lifter-caregiver or shift or venue attributes; (c) do not accommodate the statistically unbalanced nature of datasets in which MSI events are relatively rare compared to TLR occurrences that do not result in an MSI event; and/or these approaches (d) do not handle the statistically over-dispersed nature of Poisson-distributed MSI events. In some instances, the circumstances that prevent the conventional approaches and some prior art from overcoming these limitations include high-dimensionality of the attributes that characterize the risk context, such that it is not practical to obtain sufficient sample size of exposures and completed MSI events to properly statistically power quantitative determinations of the multivariable contributions to risk and MSI causation by traditional approaches. Embodiments of the present technology, which are provided in more detail below, are able to account for many of the variable and attributes that the conventional technologies could not account for. In some embodiment of the present disclosure, systems and method are provided in which context for TLR events are taken into account, which conventional technologies failed to account for. By applying the methods and systems provided herein, in some case, computing technology is improved since, for the first time, the context of historical TLR events is applied is a decision support system that improves upon the previous overly simplistic approaches by lower risk to a healthcare professional.

The conventional approaches, to solving the TLR decision-support problem addressed by embodiments of the disclosure provided herein, are overly simplistic. In particular, some of these approaches obligate designation of device or method that is needlessly castigatory and that flies in the face of logistical realities, such as the unavailability, either temporarily or for a long and unpredictable period of time, of the optimal equipment or personnel to accomplish a transfer, lift, or repositioning maneuver. Such attempts to address the problem instead create an unfavorable social and management environment, a climate wherein employees fear for recrimination for occasional policy-deviating choices that arise not out of negligence or willful nonadherence but instead out of empathetic efforts to accomplish the care of the patient in a timely manner Many times these caring and expedient choices have no adverse consequence, for the caregiver or for the patient. Some embodiments of present disclosure help to quantify the strength of those choices and create, from a large historical corpus of such events, an empirical, normative guide that can inform subsequent choices, thereby enabling caregivers: to know the usual best choice manifested by others in the precise context that they now face and, should they choose instead to deviate from that norm, to know how major or minor is the degree of their discretionary deviance and its implied attending incremental risk or cost.

Accordingly, an aim of some of the embodiments described herein is to reduce the dimensionality of explanatory variables by first discovering clusters by attributes, and to enable fast and reliable Bradley-Terry type binomial regression on the cluster-related plurality of variables, in a manner that is robust against a moderate amount of item-nonresponse or contingent missingness in the input data. Additionally, in some embodiments, a Cauchit or other link function that is robust against outliers, compared to logit, probit, and other link functions as are known to those practiced in the art may be utilized. Furthermore, a solution for identifying a plurality of models that pertain to a plurality of clusters of contexts in which MSI events are likely is also provided according to some embodiments. These examples go beyond what was contemplated by conventional technologies and provide for better decision outcomes that reduce the risk of injury to at-risk health care personnel in manners where the conventional technologies failed.

In one embodiment of the present disclosure, a system for providing an optimal transferring, lifting, and/or repositioning (TLR) modality option for a particular context to a computing device with a user interface is provided. The system comprises one or more processors; and computer-readable media having computer-usable instructions embodied thereon that, when executed by the one or more processor, cause the one or more processor to: receive raw count TLR usage information and context attributes associated with the TLR usage information; determine one or more statistical distributions that fit the TLR usage information; estimate a set of parameters for the one or more statistical distributions; determine a set of distribution quantiles for the set of parameters; based on the quantiles, transform the TLR usage information into a paired-comparison of TLR modalities; determine one or more regression models by performing model-based recursive partitioning on the context attributes, each model having a set of model coefficients; determine model convergence and model stability; for each model of the one or more regression models, determine a statistical significance for the set of model coefficients; based at least on the statistical significance for each of the one or more regression models, determine a model from the one or more regression models to be utilized in a decision-support application for determining an optimal TLR modality option for the particular context; utilize the decision-support application for determining the optimal TLR modality option for the particular context; and providing to the computing device having the user interface the optimal TLR modality option, wherein the computing device is associated with the decision-support application.

In another embodiment, one or more computer-readable media having computer-usable instructions embodied thereon that, when executed, enable a processor to perform a method for determining an optimal transferring, lifting, and/or repositioning (TLR) modality option for a particular context. The method comprises: receiving TLR usage information and context attributes for a historical population of patients and caregivers; determining one or more statistical distributions that fit the TLR usage information; estimating a set of parameters for the one or more statistical distributions; determining a distribution grouping for the set of parameters; determining one or more regression models, each model of the one or more regression models having a set of model coefficients; for each of the model of the one or more regression models, determining a statistical significance for the set of model coefficients; based on at least on the statistical significance for each model of the one or more regression models, utilizing a model from the one or more regression models in a decision-support application for determining an optimal TLR modality option for a particular context; and causing to be presented on a user interface of a device associated with the decision-support system the optimal TLR modality option.

In yet another embodiment, A computerized method for providing a transferring, lifting, and/or repositioning (TLR) option for a particular context to a user device having a user interface. The method comprises: receiving raw count TLR usage information and context attributes having a set of explanatory attribute variables, wherein the TLR usage information and context attributes are received for a historical population of caregivers that have performed TLR methods on the historical population of patients; determining one or more statistical distributions that fit the TLR usage information; estimating a set of parameters for the one or more statistical distributions; determining a distribution grouping for the set of parameters; based on the distribution grouping, transforming the TLR usage information into a paired-comparison of TLR modalities, the paired-comparison of TLR modalities having more than one possible outcome; determining one or more regression models by performing model-based recursive partitioning on the context attributes and the set of explanatory attribute variables, each model of the one or more regression models having a set of model coefficients; determining model convergence and model stability for each of the one or more regression models, wherein the model convergence and model stability is determined using a structural change method; for each model of the one or more regression models, determining a statistical significance for the set of model coefficients; based on at least on the statistical significance for each model of the one or more regression models, determining a model from the one or more regression models to be utilized in a decision-support application for determining an optimal TLR modality option for the particular context; utilizing the decision-support application for determining the optimal TLR modality option for the particular context; and providing to the computing device having the user interface the optimal TLR modality option, wherein the computing device is associated with the decision-support application.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of this disclosure including collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Environment 100 includes one or more electronic health record (EHR) systems, such as EHR system(s) 160, nursing procedures log 161, and injury records 162, communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems; and may be implemented in computer system 120. Similarly, EHR system(s) 160 may include nursing procedures log 161 and/or injury records 162, or may perform functions for these or other records systems including other EHR systems (not shown). In an embodiment, records systems 160, 161, and 162 include historical claims data for health services, apportionment data, and related health services financial data.

As shown in FIG. 1A, nursing procedures log 161 includes nursing procedures (or other caregiver procedures) related to TLR activity including equipment and methods, as well as related procedures, and may further include TLR-related event logs (e.g., logs for TLR-event activity performed by a caregiver such as turning a patient). Injury records 162 may include a subset of health records associated with caregivers or patients including injuries to caregivers occurring during the performance of their work and/or injuries incurred to patients during the course of TLR-related activity (including injury which may result from failing to move a patient soon enough).

In some embodiments of the disclosure, sequence itemset mining is performed using data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system(s) 160, procedures log 161 and/or injury records 162 include one or more data stores of health-related records, which may be stored on storage 121, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 nursing procedures log 161 and injury records 162 may further include record systems, which store real-time or near real-time patient (or user) information, such as wearable, bedside, or in-home patient monitors or sensors, for example.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient, set of patients, or provider clinicians, according to the embodiments presented herein. Embodiments of interface 142 also facilitates accessing and receiving information from a user or health care provider about a specific patient or population of patients including patient history; health care resource data; variables measurements, timeseries, and predictions (including plotting or displaying the determined outcome and/or issuing an alert) described herein; or other health-related information, and facilitates the display of results, recommendations, or orders, for example. In an embodiment, interface 142 facilitates the TLR selection decision-support tool described herein, and may further include providing the output of the determined TLR selection for a particular user/caregiver, providing instructions, as well as logging and/or receiving other feedback from the user/caregiver, in some embodiments. In an embodiment, interface 142 also facilitates receiving orders for the patient from the clinician/ user, based on the results of monitoring and predictions. Interface 142 may also be used for providing diagnostic services or evaluation of the performance of various embodiments.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on interface 142. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, interface 142 operates in conjunction with software stack 125.

In embodiments, variables mapping service 122 and records/documents ETL service 124 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126.

Computation services 126 may perform statistical or computing operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages including packages fitdistrplus, for fitting distributions; partykit, for recursive partitioning, psychotools, for psychometric modeling; and stucchange, for testing, monitoring, and dating structural changes. Computation services 126 also may include natural language processing services (not shown) such as Discern nCode™ developed by Cerner Corporation, or similar services. In an embodiment, computation services 126 include the services or routines, which may be embodied as one or more software agents or routines such as the example embodiments of computer program routines illustratively provided in FIGS. 6A-6E. In some embodiments, computation services 126 use HER system(s) 160, procedures log 161, injury records 162, and/or monitor data and model storage services 128. Monitor data and model storage services 128 may include services and programs for facilitating storage, retrieval, and implementation of the models described herein and of the data used in the models.

Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
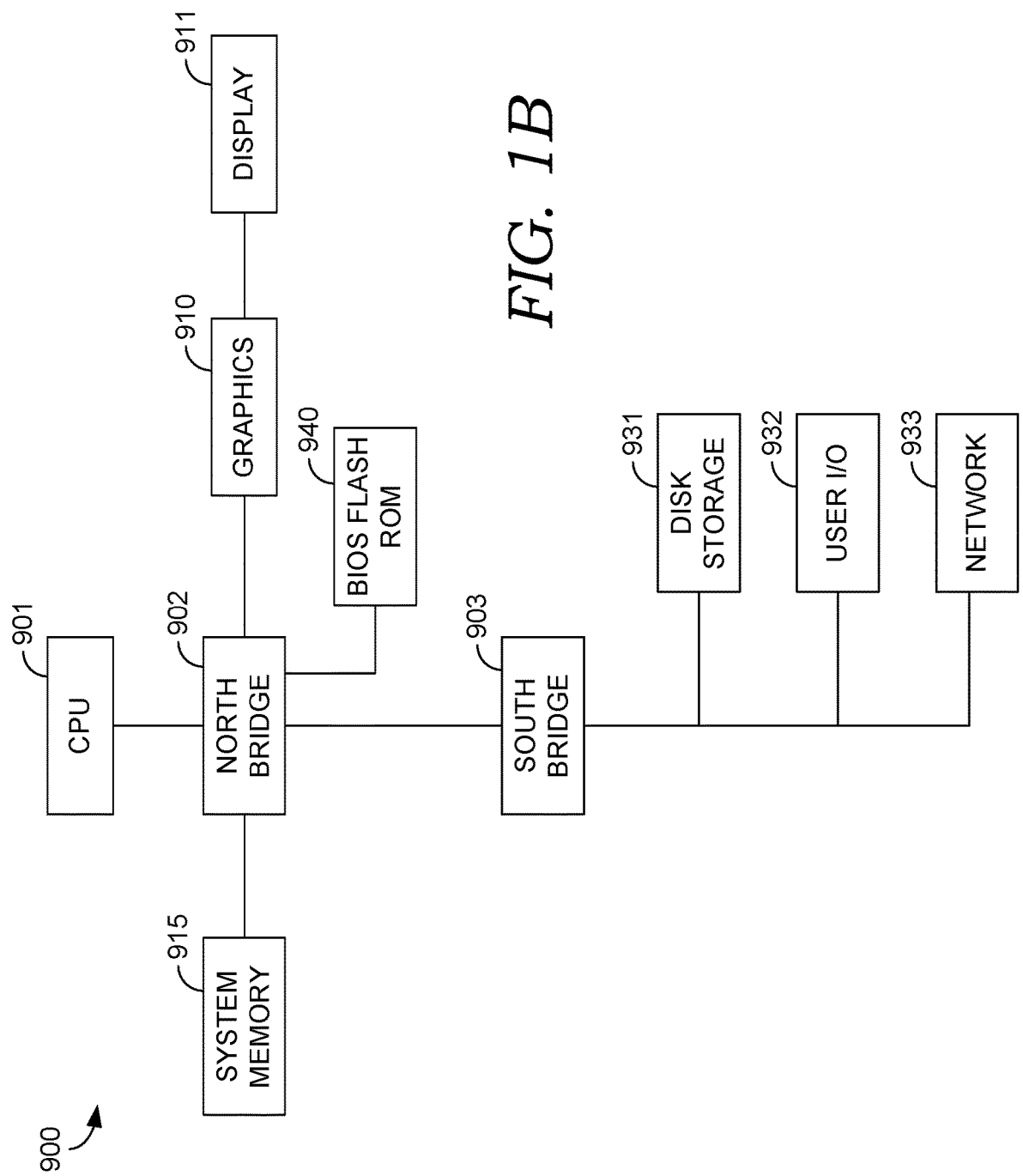

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
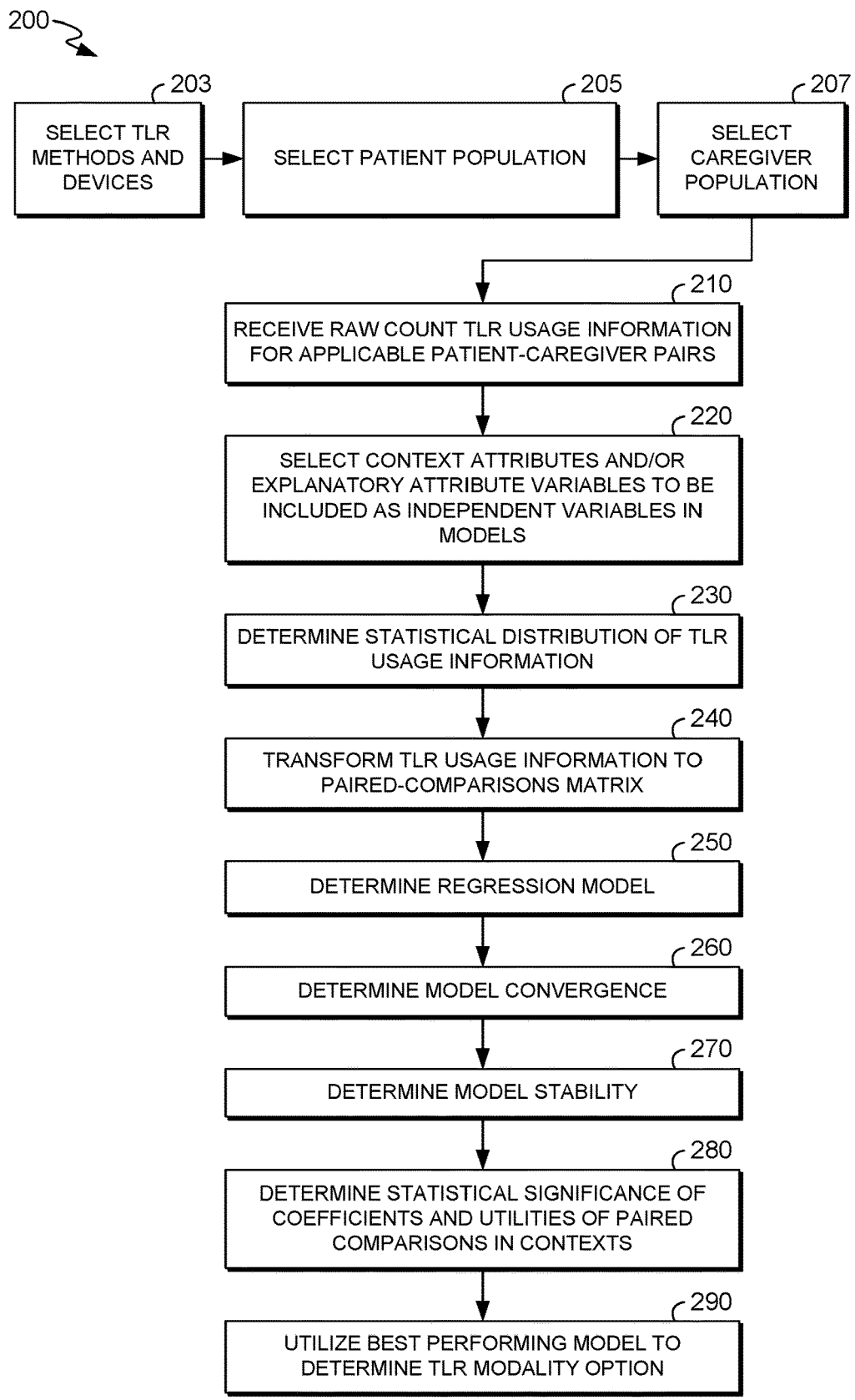
FIG. 2 depicts a flow diagram of an exemplary method for creating a TLR selection decision support tool including generating a model by performing statistical regression using Bradley-Terry regression and/or beta regression methods for paired comparisons, in accordance with an embodiment of the disclosure.

With reference now to FIGS. 2, 3A-6E, a flow diagram is provided in FIG. 2 illustrating a method 200 for creating a TLR selection decision support tool including generating a model by performing statistical regression using Bradley-Terry model-based regression and/or beta regression methods for paired comparisons. Aspects of embodiments reduced to practice based on method 200 are illustratively provided in FIGS. 3A and 3B, which depict an example table of raw counts data for TLR methods usage of devices and a table of transformed counts to a paired-comparisons matrix, respectively. The raw counts (e.g., as shown in FIG. 3A) may include TLR modalities, such as hoyer-type sling lift ("sl"), slide board, transfer mat/belt ("tr"), slippery sheet, draw sheet, stand-assist lift ("sa"), sit-to-stand lift, vs. "caregiver only" ("cg") or "lift team," and the like. The example table of transformed counts to a paired-comparisons matrix (FIG. 3B) is transformed to an ordinal scale (5th, 25th, 75th, 95th percentiles) from −2 to +2. Contestant 1 ("con1") corresponds to the patient; contestant 2 ("con2") corresponds to the caregiver; and contestant 3 ("con3") corresponds to the "playing field," such as the particular nursing unit and/or shift "conditions."

As further described herein, in some embodiments, certain aspects of TLR may be analogized to competition, such as between caregivers and patients or TLR methods and devices. The competition has a "win-lose" outcome, wherein if the caregiver is uninjured, the caregiver wins; but if the caregiver is injured, he or she loses. Similarly, if method A has prevalence greater than method B, then method A wins. Each TLR occurrence (which may be considered a particular competition) thus has context with at least three components: contestant 1 (the patient), contestant 2 (the caregiver), and the playing field (e.g., the nursing unit and/or shift conditions). Moreover, specific facts for each contestant (or the field) may correspond to points, which are used to determine the winner or loser. FIG. 4A-4C depicts example tables of "points" or weight are awarded/assigned for various patient conditions or facts related to patients, caregivers, and venue or other contextual factors.

Examples of paired-comparisons methods, which may include methods supporting the contingent presence of "ties," are now described. In each of the selected paired comparisons (which may be denoted by (j:k)) there are two possible outcomes in the ordinary case: agent j wins, jk(j), or agent k wins, jk(k). In other situations, provision is made for the possible occurrences of "ties" wherein agents j and k have identical performance, in which case there are three possible outcomes. For the analysis of such paired comparison data, a Bradley-Terry (BT) regression method is utilized. However, multivariable logistic regression, support vector machine (SVM), artificial neural network (ANN), Bayesian network, and other modeling methods are likewise capable of establishing statistical associations of explanatory variables with the "winner/loser" outcome variable, and thus these approaches may be used in some embodiments. In some instances, censoring of unlabeled cases (e.g., rows) for which the value of the outcome variable is missing is, in general, may be utilized for the model generation step. Likewise, censoring of cases (rows) in which an excessive proportion of explanatory variables' values are missing also may be utilized for the model generation step in order to produce more reliable, accurate results. Alternatively, statistical multiple imputation methods may be utilized to produce plausible, unbiased estimates or substitute values for those explanatory variables whose values are missing.

Turning now to FIG. 2 and method 200 for creating a TLR selection decision support tool including generating a model. At step 203, a set of TLR methods and devices, whose optimal assignment-in-context is to be determined, are selected. In some embodiments, the TLR methods may be selected from a set of available methods and devices, may be pre-determined, and/or may be determined based on available methods or devices, or available nurses (or other caregivers) having training in the methods and operation of the devices.

At step 205, a population of liftee-patients is selected, based on inclusion-exclusion criteria and measurement time-period. For example, the selected population may be only a single patient, or may be a group of patients, such as the patients on a particular floor or roster for a nurse (or other caregiver). Additionally, the population may comprise patients having certain weight-range (or ranges), such as patients over 250 pounds, or patients having movement restrictions, which may require specialty equipments or methods for TLR. At step 207, a population of lifter-caregivers is also selected; for example, the nurses on shift for a particular floor of bariatric patients.

At step 210, raw count TLR usage data are received for computations of the models, which may include "winner" and "loser" results for applicable patient-caregiver pairs, which may be considered to represent context attributes for the applicable prior measurement interval(s) meeting selection criteria from the preceding steps. Some embodiments of step 210 determine the raw counts from information received from records systems 160, 161, or 162 (FIG. 1A). At step 220, context attributes and/or a set of explanatory attribute variables are selected, which may be included as independent variables in the models determined at step 250 in method 200. Some context variables, known as explanatory variables, include explanatory analysis of context associated with the variable. For example, a nurse's previous injury may impact the nurse's ability to a lift patient. Some non-exclusive examples of context attributes that may be selected from are provide in FIGS. 4A-4C. In some cases context variables may be associated with the patient, such as those described in FIG. 4A, for example, patient weight, patient age, patient BMI, and the like. In some cases, context variables may be associated with a caregiver, such as those described in FIG. 4B, for example, nurse BMI, nurse history of previous injury, nurse age, and the like. In some cases, context variables may be associated with any number of additional factors. Some examples of additional factors are listed in FIG. 4C, for example, the type of unit, the caregiver to patient ratio, the length of the caregiver's shift, and so on.

Turning back to method 200 and FIG. 2, at step 230, a distribution of the TLR methods' usage data is determined. Some embodiments of step 230 comprise fitting the count TLR usage data to a statistical distribution, and may utilize the fitdistrplus R-system package of computation services 126 (described in connection to FIG. 1A). In some embodiments, Poisson, negative binomial, or similar processes may be utilized.

At step 240, the raw TLR counts are transformed into a paired comparison matrix (or similar relational data structure). In some embodiments of step 240, Efron bootstrap estimation of the distributions' parameters is performed, and distribution quantiles are determined for these estimated parameters. Further, the TLR modalities' raw usage counts may be transformed to a Likert scale based on the quantiles. For example, according to one embodiment, <5th percentile=−2; 5th to 25th percentile=−1; 25th to 75th percentile=0; 75th to 95th percentile=+1; >95th percentile=+2. Some embodiments may rescale the Likert scale to a smaller dynamic-range scale or another type of distribution grouping, if counts in some categories on the initial scale are too few. The TLR modalities usage Likert scale data is then transformed into a paired-comparisons matrix of TLR modalities to determine matches of applicable provider pairs. Further, in one embodiment, "winner"/"loser" outcomes are then rendered for applicable provider pairs. Some embodiments of step 240 may utilize the psychotools R-system package of computation services 126 (described in connection to FIG. 1A).

Figure 5A:
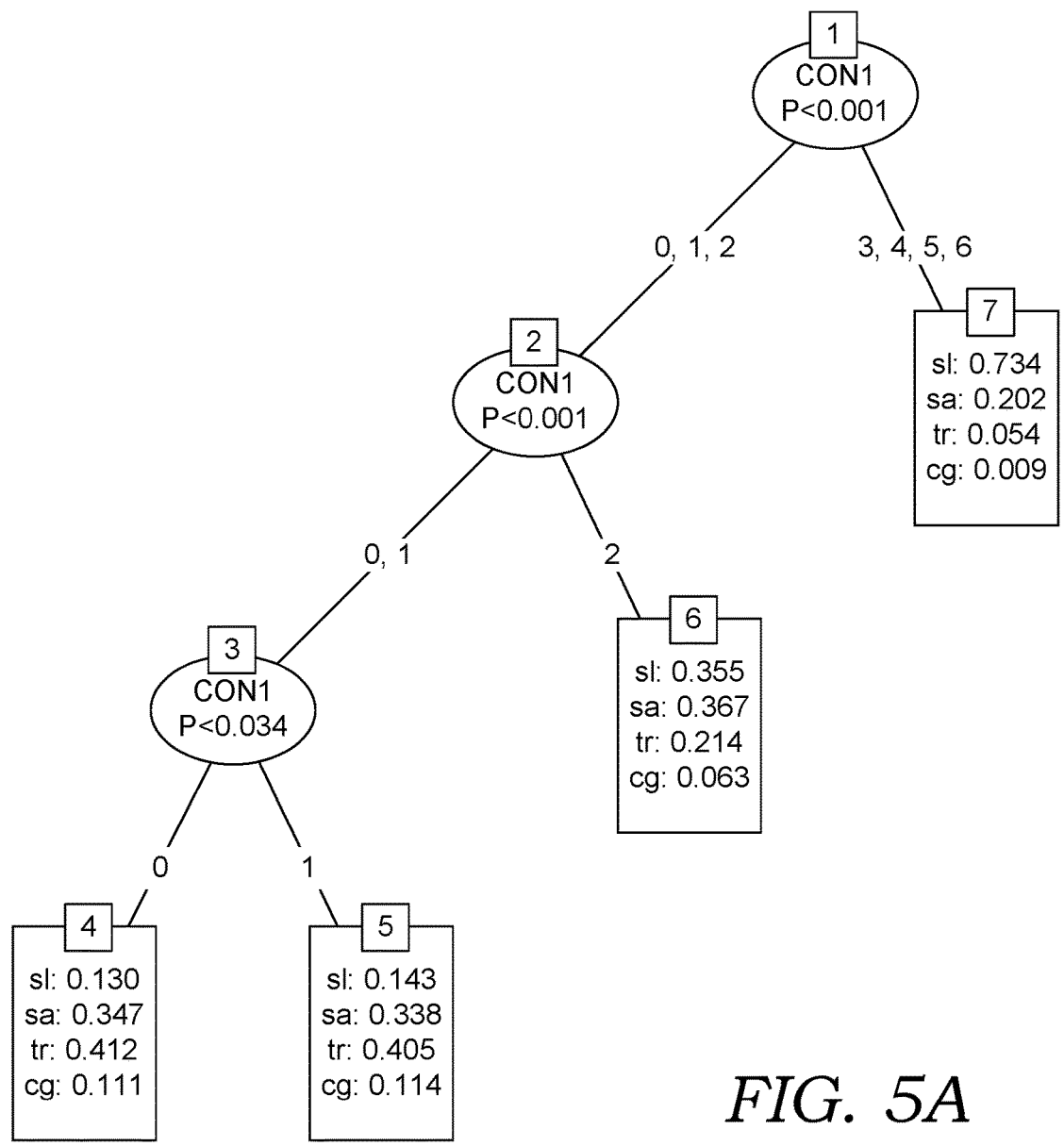
FIG. 5A provides an illustrative depiction of a model-based recursive partitioning (MOB) Bradley-Terry regression tree, in accordance with an embodiment of the disclosure.

At step 250, an optimal Bradley-Terry regression model is determined. For example, the regression model may be determined by model-based recursive partitioning on the context variables and/or the explanatory attributes variables from step 220. Alternatively, in some embodiments of method 200, a support vector machine model, neural network model, or similar appropriate model may be used in place of Bradley-Terry. Some embodiments of step 250 may utilize the partykit R-system package of computation services 126 (described in connection to FIG. 1A). FIG. 5A shows an example model-based recursive partitioning Bradley-Terry regression tree using data from an example embodiment reduced to practice (described below).

At steps 260 and 270, model convergence is determined as well as model stability, which may be determined by structural change method. Some embodiments of step 270 use the strucchange R-system package of computation services 126 (described in connection to FIG. 1A).

Figure 5B:
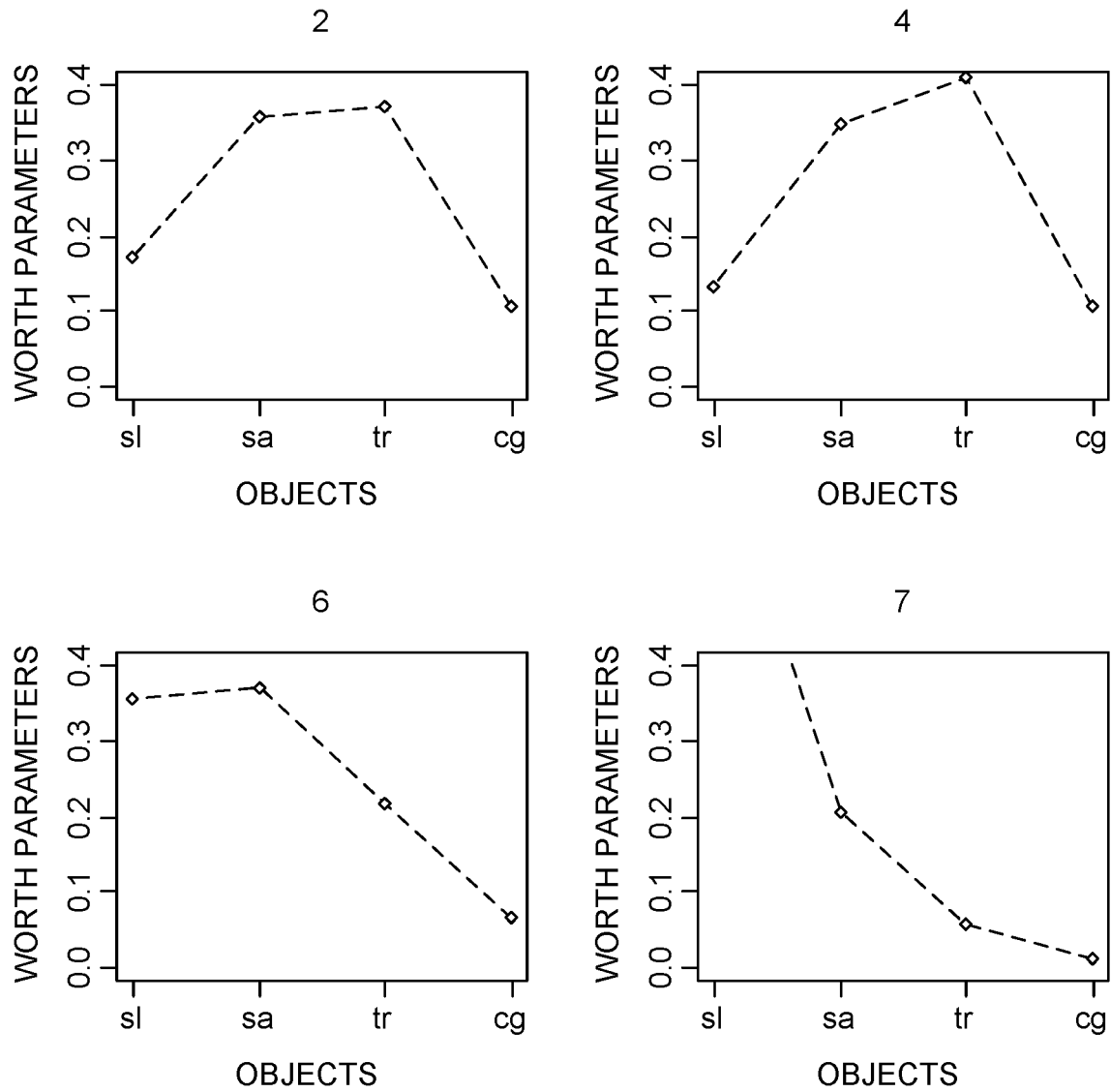
FIG. 5B depicts examples of figure-of-merit (showing "worth" and "utility") for TLR methods in the Bradley-Terry regression tree nodes, in accordance with an example embodiment reduced to practice.

At step 280, the statistical significance of the model's coefficients and utilities ("Worth") of paired-comparisons for relevant TLR modalities pairs is determined. FIG. 5B shows examples of Worth and Utility plots for the TLR methods from the Bradley-Terry regression model tree modes (determined in step 250), using data from an example embodiment reduced to practice (described below). Some embodiments of step 280 further comprise determining, from the determined statistical significance and/or utilities, the best performing model for selection criteria and contexts' explanatory variables and per-period TLR modalities' "winner"/"loser" outcomes for relevant TLR modalities pairs.

At step 290, the model and utilities determined from step 280 are incorporated into a TLR selection decision support tool. In some embodiments, this tool may comprise a stand-alone computer application or a function of another decision-support application. For example, in one embodiment a nurse/user may use the TLR-selection tool via user/clinician interface 142 of operating environment 100 (FIG. 1A) to determine the optimal method and/or equipment for performing a TLR maneuver. In some embodiments, the TLR-selection tool may, via interface 142, receive input, including contextual information, and provide an output (such as a recommended method and/or equipment) to the nurse/user. In some embodiments, a recommendation or suggestion of method/equipment may be provided automatically without user input, and further where equipment is needed, the equipment may be automatically scheduled or reserved (or in some cases transported to the right location) so that it is available for use by the nurse/user.

As described above, some embodiments of steps 230, 240, 250, and 270 may be performed using the fitdistrplus, psychotools, partykit, and stucchange R-system packages of computation services 126 (described in connection to FIG. 1A) as illustratively shown in FIG. 6A-6E. In particular, aspects of method 200, including one or more aspects of these steps may be carried out using the example computer program provided in FIGS. 6A-6E.

Additionally, some embodiments of method 200 further include generating an explanatory analysis to accompany the implemented model, for the statistically significant associations and utilities. Further, some embodiments integrate with other decision support tools and related tools, such as Cerner Millennium orders, Discern Expert CDS, iView, or similar applications. In this way, the TLR selection decision-support tool may be used by authorized nursing (or other caregiver) user(s) in selecting the best TLR modality option-in-context from among alternative TLR modalities.

Figure 7:
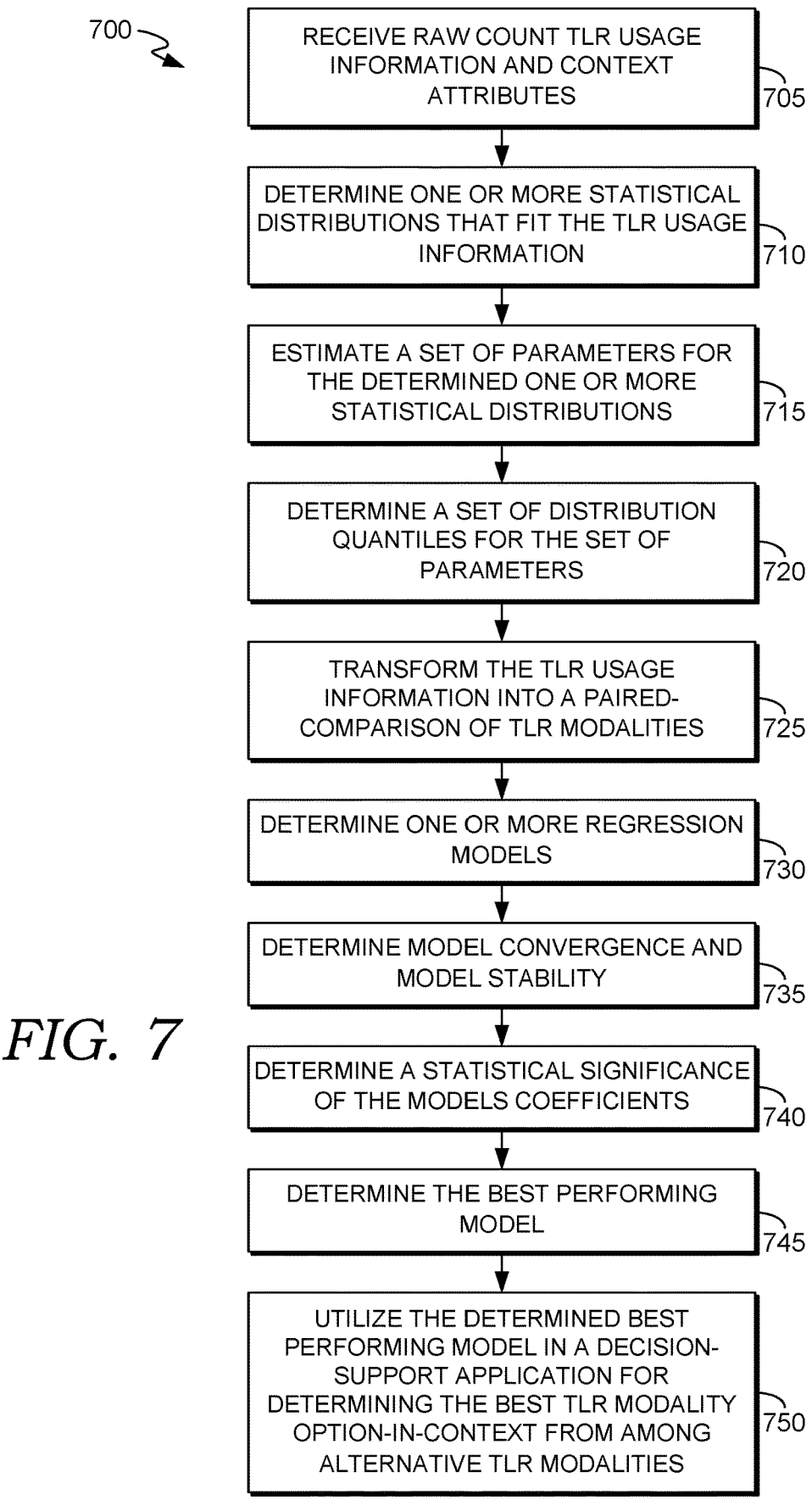
FIG. 7 is a block diagram of an exemplary method for determining a TLR modality.

Another exemplary method for determining a transferring, lifting, and/or repositioning (TLR)-selection decision support tool tailored for a particular context is provided by method 700 and FIG. 7. At step 705, raw count TLR usage information, including context attributes and/or explanatory attribute variables, is received. In some cases, weights may be assigned to the context attributes and/or the explanatory attribute variables. In some embodiments, raw count TLR usage information may include a set of available TLR methods, a population of liftee-patients, and a population of lifter-caregivers. In some embodiments, the methods and populations may be selected based on inclusion-exclusion criteria and a time period. In some aspects, the historical population of caregivers may have performed a TLR method on the historical population of patients.

At step 710, one or more statistical distributions that fit the TLR usage information are determined. In some cases, the one or more statistical distribution models may be a Bradley-Terry regression model, a support vector machine model, a neural network model, or the like. In some cases, a Poisson process or negative binomial process may be used for fitting the raw count TLR usage information to the one or more statistical distributions. At step 715, a set of parameters for the determined one or more statistical distributions is estimated. In some aspects, the estimation may be performed using Efron bootstrap estimation.

At step 720, a distribution grouping for the set of parameters is determined. In some cases, the distribution grouping may be a set of quantiles. At step 725, the TLR usage information is transformed into a paired-comparison of TLR modalities. In some cases, this may be based on the distribution groping, such as the set of quantiles. In some cases, the TLR usage information is transformed into a Likert scale, and the TLR usage information Likert scale may be transformed into a comparison's matrix of TLR modalities. In some cases, the paired-comparison of TLR modalities may be based on more than one possible outcome. For example, the paired-comparison of TLR modalities may be based on two outcomes, such as "winner"/"loser" outcomes, and in some cases, it may be based on three outcomes, such as a "winner," "loser," and "tie" outcomes.

At step 730, one or more regression models are determined. In some cases, the one or more regression models may be determined by performing model-based recursive partitioning on the context attributes and/or the explanatory attribute variables so that each model has a set of model coefficients. At step 735, model convergence and model stability is determined. In some cases, model convergence and model stability may be determined by a structural change method. At step 740, a statistical significance of the model coefficients is determined for each model of the one or more regression models. In some cases utilities of the paired-comparisons of TLR modalities are also determined. At step 745, the best performing model is determined. In some cases, the best performing model may be determined based on the statistical significance and/or the utilities of the paired-comparisons of TLR. At step 750, the best performing model is utilized to determine the best TLR modality option. In some cases the best TLR modality option may be determined in context from among alternative TLR modalities.

Example Reduction to Practice

With continuing reference to the drawings, an example embodiment reduced to practice is now described. Reduction to practice was accomplished using a computer running the Linux operating system (operating system 129), the open-source statistical software package R (software services 126), and the R packages fitdistrplus, partykit, psychotools, and strucchange, and in particular using the example computer program routine illustratively depicted in FIGS. 6A-6E.

For the reduction to practice, an observational study of was performed using de-identified, HIPAA compliant dataset from 2015 accruing at a U.S. university-based hospital. Raw counts for four example modalities of TLR (sling-type lift; stand-assist-type lift; transfer belt; unassisted caregiver lift) were transformed to quantiles by Efron bootstrap modeling of count distributions. These were then further transformed to a symmetrical Likert scale of integer values between −2 and +2 by a series of increasing thresholds of the quantile values. Bradley-Terry regression trees were fitted by a model-based recursive partitioning algorithm (MOB). Convergence of the fitting was ascertained by objective function score which ceased changing after a number of iterations, and the model with the best such score was identified. Then, model stability was determined from structural change equations, on the basis of statistical p-value. Finally, the model Bradley-Terry regression coefficients and utility values of alternative TLR modalities was determined for each of the contexts that were instantiated in the dataset of TLR usage.

Many different arrangements of the various components depicted and described, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure. For example, the following are examples of a few alternative embodiments:

Embodiment 1

A method for determining a transferring, lifting, and/or repositioning (TLR)-selection decision support tool tailored for a particular context, the method comprising: receiving information indicating raw count TLR usage data and context attributes including a set of explanatory attributes variables; fitting the TLR usage data to one or more statistical distributions; estimating a set of parameters for the one or more distributions using Efron bootstrap estimation; determining a set of distribution quantiles for the set of parameters; based on the quantiles, transforming the TLR usage data into a Likert scale; transforming the TLR usage Likert scale data into a paired-comparisons matrix of TLR modalities; determining one or more Bradley-Terry regression models by performing model-based recursive partitioning on the set of explanatory attributes variables, each model having a set of model coefficients; determining model convergence and model stability; for each model, determining a statistical significance of the models coefficients and determining utilities of paired-combinations of TLR modalities form the matrix; based on at least the determined statistical significance, determining the best-performing model; and utilizing the determined best-performing model in a decision-support application for determining the best TLR modality option-in-context from among alternative TLR modalities.

Embodiment 2

The embodiment of claim 1, wherein the raw count TLR usage data is determined from: (a) a set of available TLR methods and devices, (b) a population of liftee-patients, and (c) a population of lifter-caregivers.

Embodiment 3

Any of the above embodiments, wherein the best-performing model is further determined based on the determined utilities.

Embodiment 4

Any of the above embodiments, wherein a Poisson or negative binomial process is used for fitting the TLR usage data to a statistical distribution.

Embodiment 5

Any of the above embodiments, wherein model stability is determined by the structural change method.

Embodiment 6

Any of the above embodiments further comprising determining applicable provider pairs from the paired-comparisons matrix of TLR modalities and rendering "winner"/"loser" outcomes for the applicable provider pairs.

Embodiment 7

Any of the above embodiments further comprising selecting a subset of explanatory attributes variables to be independent variables in the one or more models, and partitioning on the subset of explanatory attributes variables.

Embodiment 8

A method for evaluating a medical therapy with a computing device, the method comprising: accessing, with the computing device, a data storage system to obtain baseline characteristics for members of a population of patients who each receive one or more transfer, lift, and/or repositioning (TLR) maneuvers administered by a caregiver; accessing, with the computing device, the data storage system to obtain baseline characteristics and information regarding members of a population of human patients and caregivers who deliver said TLR maneuvers in specific venues and contexts; accessing, with the computing device, the data storage system to obtain outcome characteristics and information regarding patients whose care was accomplished using TLR maneuvers of a plurality of modalities, methods, and lifting apparatus by a set of human caregivers, denoting which maneuvers and apparatus was used with which patients and venues and contexts by which caregivers; accessing a data storage system containing published performance statistics regarding a plurality of performance measures for selected pairs of patients and caregivers from which pairwise superior and inferior status ("winners" and "losers") of TLR modalities may be ascertained; statistically modeling the association between the TLR modalities' usage rates and the superior or inferior status of the TLR modalities in-context so as to produce rankings and utilities of said TLR modalities in-context; incorporating said statistical model and rankings and utilities into caregivers' workflow, as a means of decision-support toward timely, prospective, and automatic selection and ordering of the best TLR modality for a particular patient and contexts.

Embodiment 9

The method of embodiment 8 further comprising accessing a nursing operations and credentialing data storage system to obtain characteristics of said caregivers; and accessing a venue information data storage system to obtain characteristics of said venues and work shifts; optionally accessing a data storage system containing nursing injuries occurrence information.

Embodiment 10

Any of embodiments 8-9 further comprising analyzing the patient-provider-outcomes statistical associations by Bradley-Terry regression methods or support vector machine methods or artificial neural network modeling methods.

Embodiment 11

Any of embodiments 8-10 further comprising analyzing the patient-provider-outcomes statistical associations by model-based recursive partitioning (MOB) methods of generating a plurality of models and selecting the best from among these, where the best-performing model or regression tree is ascertained by means of an objective function score, or log-likelihood, or Akaike Information Criterion (AIC), or other means as are known to those skilled in the art.

Embodiment 12

Any of embodiments 8-11, wherein the context that characterizes risk of musculoskeletal injury (MSI) to the caregiver has a plurality of dimensions.

Embodiment 13

Any of embodiments 8-12, wherein the context has a dimensionality of at least 1 and optionally 3 or more, such as patient, caregiver, and venue dimensions.

Embodiment 14

Any of embodiments 8-13, wherein the patient context dimension is characterized by one or a plurality of component attributes, such as patient weight, patient body mass index (BMI), patient age, patient Braden score, patient Charlson comorbidity index, patient Karnofsky score, patient acuity, patient acute physiology score, patient days post-op, patient post-op delirium, patient mobilization after surgical or invasive medical procedure, patient on monitor or infusion pump or other device, patient mini mental status exam (MMSE) score, patient willingness and ability to follow instructions, patient history of fall, patient history syncope, patient major depressive disorder, patient psychosis, patient antihypertensive treatment, patient anticholinergic treatment, patient opiate treatment, patient benzodiazepine treatment, or the number of medications that the patient presently has "on-board."

Embodiment 15

Any of embodiments 8-14, wherein the caregiver context dimension is characterized by one or a plurality of component attributes, such as caregiver height, caregiver BMI, caregiver history of previous MSI, caregiver age, caregiver role (CNA, RN, NP, other), caregiver years in practice, caregiver tenure at the present institution, caregiver months in the present role, caregiver advance practice credential or graduate degree, caregiver frequency of lifts per 100 shifts, caregiver number of lift maneuvers in past 3 shifts, or caregiver working double shift.

Embodiment 16

Any of embodiments 8-15, wherein the venue context dimension is characterized by one or a plurality of component attributes, such as unit type (for example, Neuro, Orthopedics, ICU, Bariatric, etc.), unit Patient:Nurse ratio on current shift, as quantile of historical shifts, unit baseline MSI rate (injuries per year per 100 FTEs), shift (for example, Day, Evening, Night), or shift length.

Embodiment 17

Any of embodiments 8-16 further comprising calculation of net effects of attributes within a dimension (for example, by assigning integer point-values to particular attribute values and totalizing the cumulative points within a dimension, for use in subsequent determination of regression models), multinomial categorization or binomial dichotomization, Bezier or cubic spline fitting, or other mathematical transformations of variable to establish the net effect of the combinations of attributes and their values.

Embodiment 18

Any of embodiments 8-17 further comprising calculation of the parameters of a parametric distribution, such as the Poisson distribution or negative binomial distribution for the distribution of statistical values of the TLR modalities' usage raw counts during a time period.

Embodiment 19

Any of embodiments 8-18, wherein determinations of quantiles of distributions of TLR modalities' usages is accomplished by Efron bootstrap over several hundreds of iterations or similar means.

Embodiment 20

Any of embodiments 8-19, wherein threshold series of the distribution quantiles are utilized to transform TLR modalities' usage raw counts data into an ordinal (Likert) scale for subsequent analysis.

Embodiment 21

Any of embodiments 8-20, wherein ordinal values are transformed into a paired-comparisons matrix reflecting quantitative comparisons of the alternative TLR modalities.

Embodiment 22

Any of embodiments 8-21, wherein Bradley-Terry statistical regression (or support vector machine, or neural network optimization) is performed on the paired-comparisons data so as to determine a mathematical model that predicts optimal selection ('winner'/'loser' status for each applicable pair of TLR modalities in the selected context).

Embodiment 23

Any of embodiments 8-22, wherein the parallelization of the computations is performed by a cloud-based or other distributed collection comprising a plurality of processors whose joint operation is coordinated over a perhaps large physical distance via message-passing mediated by internet or other network connections.

Embodiment 24

Any of embodiments 8-23, wherein the parallelization of the computations is performed by a collection comprising a plurality of processors whose joint operation is coordinated via shared memory over modest physical distance.

Embodiment 25

Any of embodiments 8-24, wherein a plurality of mathematical models or regression trees is constructed automatically, as by model-based recursive partitioning (MOB algorithm) or like means.

Embodiment 26

Any of embodiments 8-25, wherein a statistically optimal instance model is determined from among the plurality of said constructed models.

Embodiment 27

Any of embodiments 8-26, wherein a determined optimal model is determined to have converged to a numerically stable result.

Embodiment 28

Any of embodiments 8-27, wherein equal values ("ties") for selected pairs of TLR modalities are permitted in the modeling method.

Embodiment 29

Any of embodiments 8-28, wherein model stability is determined by the statistical p-value of structural change equations.

Embodiment 30

Any of embodiments 8-29, wherein context patterns having 50 or more periods instantiated with non-zero counts in a choice category, the periods' count totals are preferably to be used as input to a programmatic distribution-fitting means, whereby the Poisson lambda rate parameter (or negative binomial distribution parameter, in the case of over-dispersed distribution where many periods have zero counts).

Embodiment 31

Any of embodiments 8-30, wherein preferably, for context patterns having fewer than 50 periods instantiated with non-zero counts in a given choice category, paired-comparisons preference scores for the applicable TLR modalities are acquired by interview with expert nurses.

Embodiment 32

Any of embodiments 8-31, wherein estimation of the quantiles of the count distributions is performed by distribution of raw counts to Poisson, negative binomial, or other appropriate distribution, followed by estimation of the quantiles of the difference between the two count variables (such as the Skellam distribution) in the case of two Poisson-distributed variables), optionally allowing for possible statistical dependence between the TLR modality raw counts.

Embodiment 33

Any of embodiments 8-32, wherein Cauchit or another link function that is robust against outliers (compared to logit, probit, or other link functions in the Bradley-Terry regression) is utilized.

It will be understood that certain features and subcombinations are of utility and may be employed without reference to other features and subcombinations and are contemplated within the scope of the claims. Not all steps listed in the various figures need be carried out in the specific order described. Accordingly, the scope of the disclosure is intended to be limited only by the following claims.

What is claimed is:

1. A system for providing an optimal transferring, lifting, and/or repositioning (TLR) modality option for a particular context to a computing device with a user interface, the system comprising:
one or more processors; and
computer-readable media having computer-usable instructions embodied thereon that, when executed by the one or more processor, cause the one or more processor to:
receive raw count TLR usage information and context attributes associated with the TLR usage information, at least a portion of the context attributes including an explanatory analysis of context associated with the variable, wherein the explanatory analysis of context associated with the variable includes a history of previous injury;
determine one or more statistical distributions that fit the TLR usage information;
estimate a set of parameters for the one or more statistical distributions;
determine a set of distribution quantiles for the set of parameters;
based on the quantiles, transform the TLR usage information into a paired-comparison of TLR modalities;
determine one or more regression models by performing model-based recursive partitioning on the context attributes, each model having a set of model coefficients;
determine model convergence and model stability;
for each model of the one or more regression models, determine a statistical significance for the set of model coefficients;
based at least on the statistical significance for each of the one or more regression models, determine a model from the one or more regression models to be utilized in a decision-support application for determining an optimal TLR modality option for the particular context;
utilize the decision-support application for automatically determining the optimal TLR modality option for the particular context; and
provide to the computing device having the user interface the optimal TLR modality option, wherein the computing device is associated with the decision-support application.

2. The system of claim 1, wherein the paired-comparison of TLR modalities comprises a comparison's matrix.

3. The system of claim 1, wherein the model convergence and the model stability are determined by a structural change method.

4. The system of claim 1, wherein the context attributes include a set of explanatory attribute variables.

5. The system of claim 1, wherein the set of parameters is estimated using Efron bootstrap estimation.

6. The system of claim 1, wherein the TLR usage information is transformed into a Likert scale, and wherein the TLR usage information Likert scale is transformed into comparison's matrix of TLR modalities.

7. The system of claim 1, wherein the one or more regression models are one of a Bradley-Terry regression model, a support vector machine model, and a neural network model.

8. The system of claim 1, wherein the TLR usage information is received for a set of available TLR methods, a population of liftee-patients, and a population of lifter-caregivers.

9. The system of claim 1, wherein the one or more processors further determine utilities of paired-combination of TLR modalities for each model of the one or more regression models, and wherein the model determined from the one or more regression modes to utilize in the decision-support application is determined at least in part based on the utilities of paired-combinations of TLR modalities.

10. The system of claim 1, wherein a Poisson process or a negative binomial process is used to determine the one or more statistical distributions that fit the TLR usage information.

11. The system of claim 1, further comprising determine applicable provider pairs from the paired-comparison of TLR modalities and rendering "winner"/"loser" outcomes for the applicable provider pairs.

12. The method of claim 11, wherein the paired-comparison of TLR modalities provides three possible outcomes.

13. One or more computer-readable media having computer-usable instructions embodied thereon that, when executed, enable a processor to perform a method for determining an optimal transferring, lifting, and/or repositioning (TLR) modality option for a particular context, the method comprising:
receiving TLR usage information and context attributes for a historical population of patients and caregivers, at least a portion of the context attributes including an explanatory analysis of context associated with the variable, wherein the explanatory analysis of context associated with the variable includes a history of previous injury;
determining one or more statistical distributions that fit the TLR usage information;
estimating a set of parameters for the one or more statistical distributions;
determining a distribution grouping for the set of parameters;
determining one or more regression models, each model of the one or more regression models having a set of model coefficients;
for each of the model of the one or more regression models, determining a statistical significance for the set of model coefficients;
based on at least on the statistical significance for each model of the one or more regression models, utilizing a model from the one or more regression models in a decision-support application for automatically determining an optimal TLR modality option for a particular context; and
causing to be presented on a user interface of a device associated with the decision-support system the optimal TLR modality option.

14. The method of claim 13, wherein weights are assigned to the contextual attributes.

15. The method of claim 13, wherein the one or more regression models are determined by performing model-based recursive partitioning on the context attributes.

16. The method of claim 13, wherein the distribution grouping is based on quantiles.

17. The method of claim 13, further comprising:
based on the distribution grouping, transforming the TLR usage information into a paired-comparison of TLR modalities; and
determining model convergence and model stability for each of the one or more regression models.

18. The method of claim 17, wherein the paired-comparison of TLR modalities comprises two or three possible outcomes.

19. A computerized method for providing a transferring, lifting, and/or repositioning (TLR) option for a particular context to a user device having a user interface, the method comprising:

receiving raw count TLR usage information and context attributes having a set of explanatory attribute variables that provide an explanatory analysis of context associated with the variable, wherein the TLR usage information and context attributes are received for a historical population of caregivers that have performed TLR methods on the historical population of patients, and further wherein the explanatory analysis of context associated with the variable includes a history of previous injury;

determining one or more statistical distributions that fit the TLR usage information;

estimating a set of parameters for the one or more statistical distributions;

determining a distribution grouping for the set of parameters;

based on the distribution grouping, transforming the TLR usage information into a paired-comparison of TLR modalities, the paired-comparison of TLR modalities having more than one possible outcome;

determining one or more regression models by performing model-based recursive partitioning on the context attributes and the set of explanatory attribute variables, each model of the one or more regression models having a set of model coefficients;

determining model convergence and model stability for each of the one or more regression models, wherein the model convergence and model stability is determined using a structural change method;

for each model of the one or more regression models, determining a statistical significance for the set of model coefficients;

based on at least on the statistical significance for each model of the one or more regression models, determining a model from the one or more regression models to be utilized in a decision-support application for determining an optimal TLR modality option for the particular context;

utilizing the decision-support application for automatically determining the optimal TLR modality option for the particular context; and providing to the computing device having the user interface the optimal TLR modality option, wherein the computing device is associated with the decision-support application.

* * * * *

UNITED STATES PATENT AND TRADEMARK OFFICE
CERTIFICATE OF CORRECTION

| | |
|---|---|
| PATENT NO. | : 11,452,652 B1 |
| APPLICATION NO. | : 15/824765 |
| DATED | : September 27, 2022 |
| INVENTOR(S) | : Douglas S. McNair |

It is certified that error appears in the above-identified patent and that said Letters Patent is hereby corrected as shown below:

On the Title Page

Under Item (56) OTHER PUBLICATIONS Column 2,
Line 5, delete "Occuprational" and insert -- Occupational --.

In the Drawings

Sheet 5 of 14, Fig. 4A, delete "INEX" and insert -- INDEX --.

In the Specification

Column 3,
Line 32, Delete "disclosure." and insert -- disclosure; --.

Column 3,
Line 55, Delete "the a" and insert -- the --.

Column 6,
Line 31, Delete "manner" and insert -- manner. --.

Column 12,
Line 4, Delete "stucchange," and insert -- strucchange, --.

Column 13,
Line 64, Delete "FIG." and insert -- FIGS. --.

Column 16,
Line 24, Delete "stucchange," and insert -- strucchange, --.

Signed and Sealed this
Twenty-fourth Day of January, 2023

*Katherine Kelly Vidal*

Katherine Kelly Vidal
*Director of the United States Patent and Trademark Office*

CERTIFICATE OF CORRECTION (continued)
U.S. Pat. No. 11,452,652 B1

Column 16,
Line 26, Delete "FIG." and insert -- FIGS. --.

In the Claims

Claim 12, Column 24, Line 16:
The line reading "The method of claim 11, wherein the paired-compari-" should read -- The system of claim 11, wherein the paired-compari- --.